United States Patent [19]

Baldwin et al.

[11] Patent Number: 5,098,707
[45] Date of Patent: Mar. 24, 1992

[54] IMIDAZOLE COMPOUNDS AND THEIR USE AS TRANSGLUTAMINASE INHIBITORS

[75] Inventors: John J. Baldwin, Gwyneed Valley; David C. Remy, North Wales; David A. Claremon, Audubon, all of Pa.

[73] Assignee: Merck & Co., Inc., Rahway, N.J.

[21] Appl. No.: 692,430

[22] Filed: Apr. 29, 1991

Related U.S. Application Data

[62] Division of Ser. No. 386,641, Jul. 31, 1989, Pat. No. 5,030,644.

[51] Int. Cl.$^5$ ............... A61K 37/547; A01N 43/52; A01N 43/50; A01N 43/00
[52] U.S. Cl. .................... 424/94.64; 514/398; 514/258; 514/161; 514/56; 514/2; 514/822
[58] Field of Search .......... 514/398, 393, 822; 424/94.64

[56] References Cited

U.S. PATENT DOCUMENTS 4,182,769  1/1980  Cherkofsky .................. 548/336
4,814,329  3/1989  Harsanyi ...................... 548/329

*Primary Examiner*—Frederick E. Waddell
*Assistant Examiner*—Gregory Hook
*Attorney, Agent, or Firm*—Alice O. Robertson; Hesna J. Pfeiffer

[57] ABSTRACT

Compositions useful for thrombolytic therapy comprising a plasminogen activator such as tPA or streptokinase together with an imidazolium salt having the formula

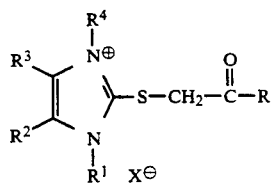

in a pharmaceutically acceptable carrier and methods for inhibiting hard clot formation or supplementing fibrinolytic therapy are described. The imidazolium salt also may be used with a platelet aggregation inhibitor or anticoagulant.

8 Claims, No Drawings

IMIDAZOLE COMPOUNDS AND THEIR USE AS TRANSGLUTAMINASE INHIBITORS

This is a division of application Ser. No. 07/386,641, filed July 31, 1989, now U.S. Pat. No. 5,030,644.

BACKGROUND OF THE INVENTION

Transglutaminases, also known as transamidases, are a family of enzymes which catalyze the amide bond formation of the γ-carboxamide group of peptide glutamine residues with an ε-amino group of peptide lysine residues.

A number of disease states have been associated with transglutaminase activity. Thus, for example, in acne lesions, transglutaminase activity in sebaceous follicles has been reported by DeYoung et. al., in J. Investigative Dermatology, 82, 275 (1984). Also, the cornified cell envelope in acne has been reported to be a result of transglutaminase activity by Dalziel et. al., Br. J. Exp. Pathology, 65, 107–115 (1984).

Another dermatological disease, psoriasis, is reported to be associated with excessive transglutaminase activity by Bernard et. al. British Journal of Dermatology, 114, 279 (1986).

Cataracts also have been reported to be associated with elevated transglutaminase activities.

Factor XIIIa is a plasma transglutaminase which is the activated form of Factor XIII also known as fibrinase or fibrin-stabilizing factor. It is essential for normal hemostatis and is responsible for the cross-linking of fibrin.

While the activity of this enzyme may be desirable and essential under most circumstances, activity under certain other circumstances can be highly undesirable. Thus, excessive thrombosis, that is the formation of clot within a blood vessel, gives rise to thrombotic strokes, deep vein thrombosis, variant angina, myocardial infarction, and other medical conditions which frequently result in necrosis of tissues and oftentimes in death of a patient. Even if death does not occur, thrombotic attacks are accompanied by damage to cells to which circulation has been prevented by thrombi formation. Removal of the thrombi by lysis is essential and the rate of lysis may be critical in ultimate patient recovery.

Lysis may occur normally in hours or days by the action of a proteolytic enzyme, plasmin, which is present in plasma as the inactive precursor, plasminogen, and which is activated by plasminogen activators, such as (pro)urokinase, urokinase or tissue plasminogen activator (tPA). Since the occurrence of a thrombotic event calls for rapid remedial action, administration of exogenous tissue plasminogen activator or (pro)urokinase is the current choice in thrombolytic or fibrinolytic therapy. However, a still further reduction in lysis time is desirable to minimize cell injury.

Since Factor XIIIa is an enzyme responsible for the final event in the coagulation of blood, lysis and maintaining the lytic state can be facilitated by the presence of a Factor XIIIa inhibitor. Moreover, the presence of a Factor XIIIa inhibitor as in a prophylactic treatment where thrombosis can be anticipated would inhibit hard clot formation. Thus, a Factor XIIIa inhibitor is useful in inhibiting thrombosis, in treating thrombosis when used with a plasminogen activator, a platelet aggregation inhibitor or anticoagulant and in post fibrinolytic therapy in maintaining the lytic state.

STATEMENT OF THE INVENTION

A novel class of imidazole compounds has been discovered which inhibits transglutaminase activity, particularly Factor XIIIa activity. The invention also embraces composition and methods for using the imidazole compounds as Factor XIIIa inhibitors in fibrinolytic or thrombolytic therapy. For use as Factor XIIIa inhibitors, the compounds may be used alone or together with agents used in thrombolytic or fibrinolytic therapy such as a plasminogen activator, a platelet aggregation inhibitor or an anticoagulant.

DETAILED DESCRIPTION OF THE INVENTION

The imidazole compounds of the present invention are selected from the group consisting of:

(A) an imidazole represented by the formula;

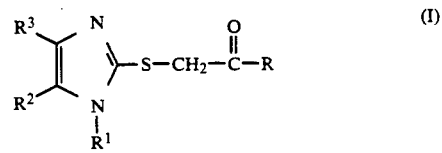

(I)

or its acid addition salt, and (B) an imidazolium salt represented by the formula;

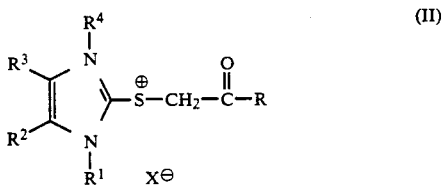

(II)

In the above and subsequent formulas:

R is
hydrogen;
lower alkyl;
substituted lower alkyl wherein the substituents are selected from hydroxy, lower alkoxy, phenoxy, phenylthio, 2-pyridinyl-N-oxide-thio, and halo;
cycloalkyl from 3 to 6 carbon atoms;
benzyl;
substituted benzyl wherein the substituents are selected from halo, hydroxy, lower alkyl and lower alkoxy;
phenyl;
substituted phenyl containing 1 to 3 substituents selected from hydroxy, lower alkoxy, carbo(lower alkoxy), carbamido, N-(lower alkyl)carbamido or cyano;
pyridyl
pyrimidinyl; or
pyrazinyl;
lower alkyl;
substituted lower alkyl wherein the substituent is carbalkoxy or carbamido; or
$ArC_nH_{2n}$- wherein Ar is phenyl, (lower alkyl)phenyl, (lower alkoxy)phenyl, or halophenyl and n is 1–3;

$R^2$ is
nitro;
carbo(lower alkoxy);
halo;
cyano;

phenyl;
substituted phenyl containing from 1 to 3 substituents selected from lower alkyl, lower alkoxy, halo, and hydroxy;
phenoxy;
phenylthio;
an amido group represented by
—NHCOQ wherein Q is lower alkyl,
—CH(NH$_2$)CH$_2$C$_6$H$_5$ or —NH(lower alkyl);
a hydroxyalkyl group represented by

wherein R' is hydrogen or R" wherein R" is hydrogen, phenyl, phenoxyphenyl, biphenylyl, (lower alkyl)phenyl, lower alkyl and lower cycloalkyl, or R' and R" taken together is alkylene from 4 to 6 carbon atoms; or
an ether-alkyl group represented by

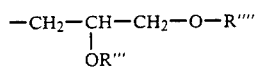

wherein
R''' is hydrogen, —CO-(lower alkyl),
—CO-phenyl, —CO-biphenylyl,
—CO-phenyl-O-phenyl and —CONH-phenyl, and
R'''' is phenyl or lower alkyl;
R$^3$ is hydrogen, or when R$^2$ is phenyl or substituted phenyl is optionally the same as R$^2$; or
R$^2$ and R$^3$ taken together may be alkylene from 3 to 10 carbon atoms optionally substituted with phenyl or spiroalkylene, or benzo;
R$^4$ is lower alkyl, ArC$_n$H$_{2n}$ wherein Ar is phenyl, (lower alkyl)phenyl, (lower alkoxy)phenyl, or halophenyl, and n is 1-3; and
X is an anion of a pharmaceutically acceptable salt.

By the expressions "lower alkyl" and "lower alkoxy" as employed in the specification and claims are meant radicals having from 1 to 6 carbon atoms.

By the expression "spiroalkylene" is meant an alkylene chain of from 3 to 6 carbon atoms, the end carbons of which are attached to the same carbon of the nucleus.

By the expression "halo" is meant fluoro, chloro, bromo and iodo.

Pharmaceutically acceptable salts suitable as acid addition salts as well as providing the anion of the imidazolium salts are those from acids such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethanesulfonic, trifluoromethanesulfonic and the like, and include other acids related to the pharmaceutically acceptable salts listed in Journal of Pharmaceutical Science, 66, 2 (1977) and incorporated herein by reference.

The compounds, both those which are acid addition salts of the compounds represented by formula (I) and those quaternary salts represented by formula (II) are solids soluble in polar solvents such as water, methanol, ethanol and the like. The imidazoles of formula (I) are soluble in non-polar solvents such as ethyl acetate, methylene chloride, ethylene dichloride, carbon tetrachloride, and the like.

The compounds of the present invention are useful as transglutaminase inhibitors, particularly as Factor XIIIa inhibitors, and are adapted to be employed in thrombolytic therapy. In such use, it is administered to a thrombotic patient susceptible to thrombotic attack either alone or in combination with an antithrombotic agent.

Preferably, it is employed together with a plasminogen activator, an enzyme which converts plasminogen to plasmin to increase the rate and extent of lysis. Suitable activators include tissue plasminogen activator (tPA), prourokinase (single chain urokinase), urokinase (dual chain urokinase), streptokinase and eminase (European patent application 028,489). The plasminogen activators may be those isolated from natural sources or produced by recombinant technology and include the genetically engineered variants thereof.

Also, it may be employed together with platelet aggregation inhibitors. Platelet aggregation inhibitors may be drugs, naturally occurring proteins or peptides or may be modified or semi-synthetic proteins or peptides. Established drugs which are platelet aggregation inhibitors include aspirin and dipyridamole. Proteins or polypeptides which are platelet aggregation inhibitors have a certain peptide sequence, most frequently Arg-Gly-Asp. Some classes of natural proteins having this property are fibrinogen receptor antagonists, thromboxane receptor antagonists, thromboxane synthesis inhibitors, collagen receptor antagonists and thrombin inhibitors. Among especially useful polypeptides are those designated "Echistatin" and "Bitistatin" and having the amino acid sequence: X-Cys-R-R-R-Arg-Gly-Asp-R-R-R-R-R-Cys-Y where X is H or an amino acid, Y is OH or an amino acid and each R independently is an amino acid, described and claimed in copending applications Ser. No. 184,649, filed Apr. 22, 1988; Ser. No. 303,757, filed Feb. 1, 1989; and Ser. No. 307,642 filed Feb. 7, 1989, all in the names of P. A. Friedman, et. al., the teachings of which are incorporated by reference.

Additionally, the imidazole compounds may be employed for continued therapy after initial relief from thrombotic attack thereby providing a more complete lysis and minimizing complications from reocclusion. Moreover, the imidazole compounds may be employed in post thrombosis therapy together with anticoagulants such as heparin and coumarin drugs.

The preferred compounds for use as transglutaminase inhibitors are the quaternary imidazolium salts.

The compounds of the present invention which are imidazoles may have additional utility as intermediates in one method of preparation of the preferred imidazolium salts.

The imidazoles (I) useful in the present invention may be prepared according to the following equation (1). (In a subsequent table, this method is referred to as Method A).

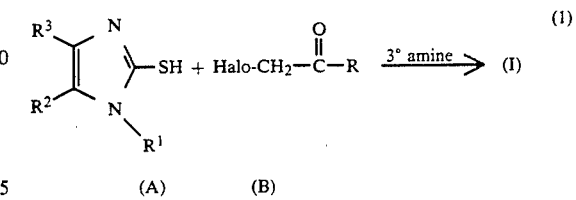

In the preparation of the imidazole of formula (I), the 2-mercaptoimidazole (A) starting material, which may be prepared by known procedures hereinafter detailed, is intimately contacted with and caused to react with an acylmethyl halide (B) in the presence of a tertiary amine (3° amine) in an organic solvent at ambient temperature for time sufficient for reaction to take place with the formation of the desired imidazole of formula (I). After completion of the reaction, the imidazole may be recovered from the reaction mixture by removing the solvent by evaporation and purifying the residue by conventional procedures.

Tertiary amines suitable in the reaction include triethylamine, trimethylamine, pyridine, picolines, collidines, and the like.

Suitable solvents for the reaction include acetone, methyl ethyl ketone, dimethylformamide, dimethyl sulfoxide and the like.

In carrying out the reaction, a solution of the acylmethyl halide is added to a solution of the 2-mercaptoimidazole and tertiary amine and the mixture stirred at room temperature for several hours, conveniently overnight. At the end of this period, the solvent is evaporated and the residue partitioned between water and a water-immiscible organic solvent such as ethyl acetate. The organic solution containing the imidazole is washed and dried, the imidazole recovered from the dried solution as residue, and thereafter, purified, preferably by chromatography on silica gel using methanol/chloroform as eluant.

The imidazole then may be employed in the therapeutic method of the present invention as such or as an acid addition salt, or may be treated as an intermediate and employed in the preparation of the imidazolium salts.

The acid addition salts may be prepared in a conventional manner such as by intimately mixing the imidazole and desired acid, preferably in a minimal amount of polar solvent such as ethanol or by other conventional procedures.

The imidazolium salts may be prepared according to the following equation (2).

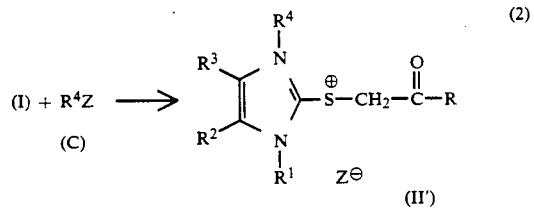

wherein Z is a displaceable group of an active quaternizing agent, and within the definition of X. The reaction is carried out by intimately contacting the reactants in a solvent at ambient temperature for a time sufficient for the reaction to take place with the formation of an imidazolium salt (II′). The imidazolium salt (II′) may be recovered by conventional procedures and purified, if desired, or converted to the ultimate imidazolium salt by use of an anion exchange resin:

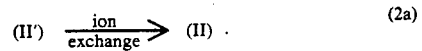

The quaternizing agent is preferably alkyl trifluoromethanesulfonate or other active agent. The halide salts and many other salts are preferably prepared from the trifluoromethanesulfonate.

The reaction may be carried out for from as little as about two hours to a week or so, depending on the particular reactants.

In carrying out the reaction, methyl trifluoromethanesulfonate is added to a solution of the appropriate imidazole (I) in an aprotic organic solvent such as methylene chloride and the resulting mixture stirred at ambient temperature for time sufficient for substantial completion of the reaction. At the end of this period, the solvent is vaporized and the residue crystallized to obtain the trifluoromethanesulfonate salt or is converted into a halide by ion-exchange chromatography, using alkanol/water as eluant. The resulting imidazolium salt is recovered from the eluate and purified, if desired, by conventional procedures.

The imidazolium compound represented by formula (II) may be prepared by an alternate procedure in which a 1,3-disubstituted-imidazoline-2-thione is the starting material. This method may be used when X is halogen and in such a case, a 1,3-disubstituted-imidazoline-2-thione is caused to react with an acylmethyl halide according to the following equation: (In a subsequent table, this method is referred to as Method (B)).

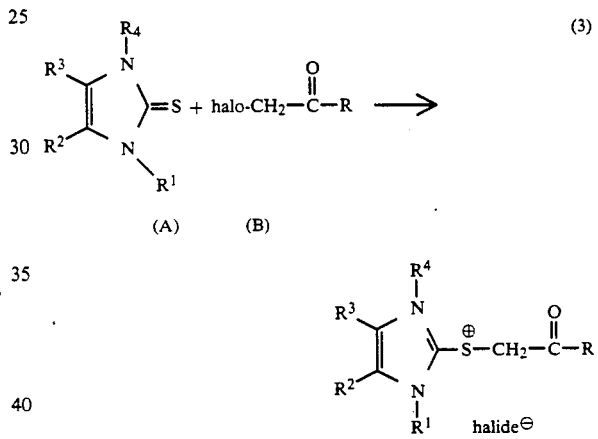

The thione starting material may be prepared as subsequently described or by any alternate procedure known to those skilled in the art. It may be prepared as a first step and the alkanoylmethyl halide added to the reaction mixture.

In the foregoing reaction of the thione and the acylmethyl halide, about equimolar amounts of the reactants are employed and the reaction is carried out in solution. Solvents suitable for carrying out the reaction are acetone, methyl ethyl ketone and the like. The reaction may be carried out between about 20° to about 50° C. over a period of from about 4 to about 24 hours. Conveniently, the reaction may be carried out by stirring overnight. The reaction may be catalyzed by the addition of a small crystal of sodium iodide.

In carrying out the reaction, the acylmethyl halide (B) is added to a solution of the imidazoline-2-thione (A) and the resulting mixture stirred together for time sufficient to complete the reaction with the formation of the desired imidazolium salt which precipitates in the reaction mixture. The imidazolium salt product may be recovered and purified by conventional procedures.

The imidazolium salts in which $X^-$ is halide may be converted to salts in which $X^-$ is trifluoromethanesulfonate or other anions by charging an ion-exchange column with the sodium salt of trifluoromethanesulfonate or other desired anion in a conventional manner. Thereafter, the imidazolium halide is charged on the column in a solvent such as methanol and the desired imidazolium salt recovered from the eluate by vaporizing off the solvent.

The usefulness of the compounds as Factor XIIIa inhibitors for enhancing the rate of clot lysis catalyzed by plasminogen activators may be demonstrated first by establishing the inhibitory potencies of the compounds in a Factor XIIIa assay.

The Factor XIIIa inhibitor assay is based on the incorporation of $^{14}C$-putrescine into casein catalyzed by Factor XIIIa. The assay is carried out employing the procedure described in Methods in Enzymology, Vol. 45, Ch 15., pages 177-191 (1976) and using Factor XIII (F XIII) isolated from human plasma. The procedure is summarized briefly and schematically illustrated as follows:

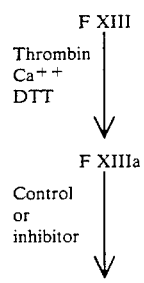

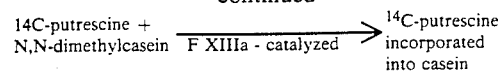

Factor XIII assay mixtures are prepared by adding stepwise, appropriately prepared solutions of thrombin and dithiothreitol (DTT) to a mixture comprising Factor XIII at 140 mg/mL in glycerol/water and tris(hydroxymethyl)aminomethane hydrochloride (Tris.HCl). To a portion of the mixture is added calcium chloride as source of calcium ions required for enzyme activity and to the remaining mixture is added, instead of calcium ions, ethylenediaminetetraacetic acid (EDTA) which serves as a blank for background.

A substrate mixture is prepared from $^{14}C$-putrescine and N,N-dimethylcasein.

The assay tubes and control tubes are charged with the substrate mixture and incubated at 37° C. for 20 minutes. Samples are withdrawn from each tube, spotted onto a filter disk which is then immersed in ice cold trichloroacetic acid solution to precipitate the casein on the filter. The filter is then washed to remove unincorporated or free $^{14}C$-putrescine and after drying is counted for $^{14}C$-putrescine incorporated to casein from which percent activity and/or inhibition can be calculated.

Imidazole compounds showing at least 50 percent activity at $2\times10^{-5}M$ in the Factor XIIIa assay are considered to be useful in inhibiting hard clot formation or especially in supplementing fibrinolysis by plasminogen activator.

The imidazoles and imidazolium salts seen in Table I are representatives of compounds having $IC_{50}$ at concentrations below $2\times10^{-5}M$. Also seen in Table I are the properties of the various compounds.

TABLE I $$\begin{array}{c}\text{Structure:}\\ R^4-N\cdots C(-S^{\oplus}-CH_2-C(=O)-R)\cdots N-R^1 \\ \text{with ring carbons bearing } R^3 \text{ and } R^2,\ X^{\ominus} \text{ counterion}\end{array}$$

| Comp. No. | Method of Preparation | R | R¹ | R² | R³ | R⁴ | Salt or Anion(X⁻) | M.P. °C. |
|---|---|---|---|---|---|---|---|---|
| 1 | A | —CH₃ | —CH₃ | —NO₂ | —H | —CH₃ | CF₃SO₃⁻ | 96–97° |
| 2 | A | —CH₃ | —CH₃ | —COOCH₃ | —H | —CH₃ | CF₃SO₃⁻ | 106–108° |
| 3 | A | —CH₃ | —CH₂CH₂COOCH₃ | —H | —H | —CH₃ | Cl⁻ | 121–124° |
| 4 | A | —CH₃ | —CH₂CH₂CONH₂ | —H | —H | —CH₃ | Cl⁻ | 124–125° |
| 5 | A | —CH₃ | —CH₃ | —COOCH₃ | —H | — | — | 117.5–118° |
| 6 | A | —CH₃ | —CH₃ | —NO₂ | —H | — | — | 86–87.5° |
| 7 | A | —CH₃ | —CH₃ | —CH₂OH | —H | — | — | 69–71° |
| 8 | A | —CH₃ | —CH₃ | —CH₂OH | —H | —CH₃ | Cl⁻ | foam |
| 9 | A | —CH₃ | —CH₃ | —C₆H₅ | —C₆H₅ | —CH₃ | CF₃SO₃⁻ | 138–139° |
| 10 | B | —CH₃ | —CH₂C₆H₅ | —H | —H | —CH₃ | Cl⁻ | 119–121° |
| 11 | A | —CH₃ | —CH₃ | —C₆H₅ | —H | —CH₃ | Cl⁻ | 143–146° |
| 12 | A | —CH₃ | —CH₃ | (o-tolyl fused/phenyl) | —H | —CH₃ | CF₃SO₃⁻ | 130–132° |
| 13 | A | —CH₃ | —CH₃ | (o-tolyl fused/phenyl) | — | — | — | 87–88° |
| 14 | B | —CH₃ | —CH₃ | —Cl | —H | —CH₃ | Cl⁻ | 134–136° |
| 15 | A | —CH₃ | —CH₃ | —C₆H₅ | —C₆H₅ | — | .HCl | 179–182° |
| 16 | A | —CH₃ | —CH₃ | —C₆H₅ | —H | — | — | 69.5–71° |
| 17 | A | —CH₃ | —CH₃ | —CHC₆H₅ / —OH | H | —CH₃ | Cl⁻ | oil |
| 18 | A | —CH₃ | —CH₃ | —C(C₆H₅)₂ / —OH | H | —CH₃ | Cl⁻ | 164–165°(dec) |

TABLE I-continued
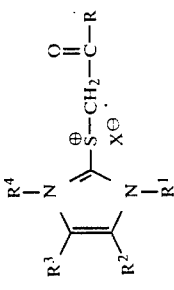
| Comp. No. | Method of Preparation | R | R¹ | R² | R³ | R⁴ | Salt or Anion(X⁻) | M.P. °C. |
|---|---|---|---|---|---|---|---|---|
| 19 | A | —CH₃ | —CH₃ | cyclohexyl-S-OH | H | —CH₃ | CF₃SO₃⁻ | 100°(dec) |
| 20 | B | —CH₃ | —CH₃ | 4-CH₃-C₆H₄-C(CH₃)₂-OH | H | —CH₃ | Cl⁻ | 72–76° |
| 21 | B | —CH₃ | —CH₃ | 3-CH₃-C₆H₄-C(CH₃)₂-OH | H | —CH₃ | Cl⁻ | 72–78° |
| 22 | B | —CH₃ | —CH₃ | 2-CH₃-C₆H₄-C(CH₃)₂-OH | H | —CH₃ | Cl⁻ | 74–81° |
| 23 | A | —CH₃ | —CH₃ | —C(CH₃)(C(CH₃)₃)—OH | H | — | — | 128.5–130.5° |
| 24 | A | —CH₃ | —CH₃ | —C(CH₃)(C(CH₃)₃)—OH | H | —CH₃ | CF₃SO₃⁻ | 67–72° |

TABLE I-continued $$\begin{array}{c} R^4 \\ | \\ N \\ \oplus \\ R^3 \end{array} \begin{array}{c} O \\ \| \\ S-CH_2-C-R \\ X^\ominus \\ | \\ R^1 \end{array}$$

| Comp. No. | Method of Preparation | R | R¹ | R² | R³ | R⁴ | Salt or Anion(X⁻) | M.P. °C. |
|---|---|---|---|---|---|---|---|---|
| 25 | B | —CH₃ | —CH₃ | —NHCNHCH₃<br>‖<br>O | H | —CH₃ | Cl⁻ | 177–179° |
| 26 | B | —CH₃ | —CH₃ | —CH₂CHCH₂OC₆H₅<br>\|<br>OH | H | —CH₃ | CF₃SO₃⁻ | 82–84° |
| 27 | B | —CH₃ | —CH₃ | —NHCCH₃<br>‖<br>O | H | —CH₃ | Cl⁻ | 171–173° |
| 28 | B | —CH₃ | —CH₃ | —SC₆H₅ | H | —CH₃ | Cl⁻ | 115–119° |
| 29 | A | —CH₃ | —CH₃ | —CH₂CHCH₂OC₆H₅<br>\|<br>OCOCH₃ | H | —CH₃ | CF₃SO₃⁻ | 88–90°(dec) |
| 30 | A | —CH₃ | —CH₃ | —(CH₂)₄— | | — | 54–56° |
| 31 | B | —CH₃ | —CH₃ | —CH₂CHCH₂OCH₃<br>\|<br>OCOC₆H₅ | H | —CH₃ | Cl⁻ | oil |
| 32 | B | —CH₃ | —C₂H₅ | —(CH₂)₄— | | —C₂H₅ | Cl⁻ | 94–96° |
| 33 | A | —CH₃ | —CH₃ | —(CH₂)₁₀— | | — | | 88–89° |
| 34 | B | —CH₃ | —CH₃ | —CH₂CHCH₂OC₆H₅<br>\|<br>CONHC₆H₅ | H | —CH₃ | Cl⁻ | 81–89° |
| 35 | A | —CH₃ | —CH₃ | —CH—C₆H₄C₆H₅<br>\|<br>OH | H | — | — | 62–69° |
| 36 | A | —CH₃ | —CH₃ | —CH—C₆H₄C₆H₅<br>\|<br>OH | H | —CH₃ | Cl⁻ | 127–130° |

TABLE I-continued $$\begin{array}{c} R^4 \\ | \\ N \\ \end{array} \overset{\oplus}{\underset{\ominus}{S}} - CH_2 - \overset{O}{\underset{\|}{C}} - R \\ X^{\ominus}$$

| Comp. No. | Method of Preparation | R | R¹ | R² | R³ | R⁴ | Salt or Anion(X⁻) | M.P. °C. |
|---|---|---|---|---|---|---|---|---|
| 37 | A | —CH₃ | —CH₃ | —(CH₂)₄— | | —CH₃ | Cl⁻ | 88-91° |
| 38 | A | —CH₃ | —CH₃ | —CH₂CHCH₂OCH(CH₃)₂<br>OCOC₆H₅ | H | —CH₃ | CF₃SO₃⁻ | 84-86° |
| 39 | B | —CH₃ | —CH₃ | —CH₂CHCH₂OCH(CH₃)₂<br>OCONHC₆H₅ | H | —CH₃ | Cl⁻ | oil |
| 40 | B | —CH₃ | —CH₃ | —CH₂CHCH₂OCH(CH₃)₂<br>OH | H | —CH₃ | Cl⁻ | oil |
| 41 | B | —CH₃ | —CH₃ | —CH₂—⌬—O—⌬—OH | H | —CH₃ | Cl⁻ | 118-123° |
| 42 | B | —CH₃ | —CH₃ | —CH₂—⌬—O—⌬—OH (meta) | H | —CH₃ | Cl⁻ | 73-81° |
| 43 | B | —CH₃ | —CH₃ | —NHCOCHCH₂C₆H₅<br>NH₂ | H | —CH₃ | Cl⁻ | FOAMS<br>90-100° |
| 44 | B | —CH₃ | —CH₃ | —⌬—OCH₃ | —⌬—OCH₃ | —CH₃ | Cl⁻ | 179-180° |

TABLE I-continued

![structure: R^4-N=C(S-CH2-C(=O)-R)(X^⊖)-N(R^1)-... with R^2, R^3 on ring]

| Comp. No. | Method of Preparation | R | R¹ | R² | R³ | R⁴ | Salt or Anion(X⁻) | M.P. °C. |
|---|---|---|---|---|---|---|---|---|
| 45 | B | —CH₃ | —CH₃ | —(CH₂)₄— | | —CH₃ | Cl⁻ | 73–78° |
| 46 | A | —CH₃ | —CH₃ | —CH₂CHOCOC₆H₄C₆H₅(p)<br>CH₃OCH(CH₃)₂ | H | —CH₃ | CF₃SO₃⁻ | 101–102.5 |
| 47 | A | —CH₃ | —CH₃ | —CH₂CHOCOC₆H₄C₆H₅(o)<br>CH₂OCH(CH₃)₂ | H | —CH₃ | CF₃SO₃⁻ | 60–62 |
| 48 | A | —CH₃ | —CH₃ | —CH₂CHOCOC₆H₄OC₆H₅(o)<br>CH₂OCH(CH₃)₂ | H | —CH₃ | CF₃SO₃⁻ | 54–56.5° |
| 49 | B | —CH₃ | —CH₃ | —CH(S-cyclohexyl)-OH | H | —CH₃ | Cl⁻ | 61–81° |
| 50 | A | —CH₃ | —CH₃ | —CH₂—CHOCOC₆H₅<br>CH₂OC₆H₅ | H | —CH₃ | Cl⁻ | 61–70° |
| 51 | A | —CH₃ | —CH₃ | —CH₂CHOCOC₆H₄C₆H₅(p)<br>CH₂OC₆H₅ | H | —CH₃ | CF₃SO₃⁻ | 122–125° |
| 52 | A | —CH₃ | —CH₃ | —CH₂CHOCOC₆H₄C₆H₅(o)<br>CH₂OC₆H₅ | H | —CH₃ | CF₃SO₃⁻ | 53–66° |
| 53 | A | —CH₃ | —CH₃ | —CH₂CHOCOC₆H₄C₆H₅(o)<br>CH₂OH | H | —CH₃ | Cl⁻ | 75–81° |
| 54 | B | —CH₃ | —CH₃ | —C₆H₅Cl(p) | —C₆H₅Cl(p) | —CH₃ | Cl⁻ | Hygroscopic |
| 55 | B | —CH₃ | —CH₃ | —(CH₂)₃— | | —CH₃ | Cl⁻ | Hygroscopic |

TABLE I-continued

| Comp. No. | Method of Preparation | R | $R^1$ | $R^2$ | $R^3$ | $R^4$ | Salt or Anion($X^-$) | M.P. °C. |
|---|---|---|---|---|---|---|---|---|
| 56 | B | —$CH_3$ | —$CH_3$ | —$CH_2$—$\overset{\displaystyle C_6H_{11}}{\underset{\displaystyle }{C}}$—$CH_2$— | | —$CH_3$ | $Cl^-$ | 124–127° |
| 57 | A | —$CH_3$ | —$CH_3$ | —$CH_2$—CH—$CH_2$—<br>$\qquad\quad\ \, $|<br>$\qquad\quad\ \,C_6H_5$ | | —$CH_3$ | $CF_3SO_3^-$ | 137–139° |
| 58 | B | —$CH_3$ | —$CH_3$ | —$CH_2$—CH—$CH_2$—$CH_2$—<br>$\qquad\quad\ \, $|<br>$\qquad\quad\ \,C_6H_5$ | | —$CH_3$ | $Cl^-$ | 76–91° |
| 59 | B | —$CH_3$ | —$CH_3$ | —$CH_2$—C($CH_3$)$_2$—$CH_2$— | | —$CH_3$ | —$Cl^-$ | 95–97° |
| 60 | A | —$CH_3$ | —$CH_3$ | —$CH_2CHCH_2OC_6H_5$<br>$\quad\ \, $|<br>$\quad\ \,OCOC_6H_5$ | H | —$CH_3$ | $Cl^-$ | –61–70° |
| 61 | A | —$CH_3$ | —$CH_3$ | —$CH_2CH$—$CH_2OC_6H_5$<br>$\quad\ \, $|<br>$\quad\ \,OH$ | —$CH_3$ | —$CH_3$ | $Cl^-$ | 69–76° |
| 62 | A | —$CH_3$ | —$CH_3$ | 4-($HO$)($CH_3$)$C$-$C_6H_4$- (p-cumyl-OH group) | —$CH_3$ | —$CH_3$ | $CF_3SO_3^-$ | 113–115° |
| 63 | A | —$CH_3$ | —$CH_3$ | —$CH_2CH$—$CH_2OC_6H_4C_6H_5(o)$<br>$\quad\ \, $|<br>$\quad\ \,OH$ | —$CH_3$ | —$CH_3$ | $CF_3SO_3^-$ | 50–57° |
| 64 | B | —$CH_3$ | —$CH(CH_3)_2$ | —$(CH_2)_4$— | | —$CH(CH_3)_2$ | $Cl^-$ | 108–110° |

TABLE I-continued

![Structure: pyrimidine ring with R⁴-N, N-R¹, R²-, R³- substituents, and S⁺-CH₂-C(=O)-R group with X⁻ counterion]

| Comp. No. | Method of Preparation | R | R¹ | R² | R³ | R⁴ | Salt or Anion(X⁻) | M.P. °C. |
|---|---|---|---|---|---|---|---|---|
| 65 | A | —CH₃ | —CH₃ | H | —CH₂—CHCH₂CH₂— with CH₃ | —CH₃ | Cl⁻ | oil |
| 66 | A | —C₆H₅ | —CH₃ | H | H | —CH₃ | CF₃SO₃⁻ | 167-169°(dec) |
| 67 | A | 3-(C(=O)NHCH₂C₆H₅)-C₆H₄ | —CH₃ | H | H | H | I⁻ | 119.5-121° |
| 68 | A | 3-(COOCH₃)-C₆H₄ | —CH₃ | H | H | —CH₃ | I⁻ | 106-109° |
| 69 | A | —CH₃ | —CH₃ | —CH₃ | —CH₃ | —CH₃ | Cl⁻ | 114-115°(hydrate) |

For use in facilitating or supplementing fibrinolytic therapy, the imidazole compound may be administered in a pre- or post-lytic state alone or in combination therapy. Preferably, it is used in a combination therapy with a plasminogen activator, with a platelet aggregation inhibitor or with natural and synthetic anticoagulants.

The process for facilitating or supplementing fibrinolytic therapy in prothrombic patients comprises administering a therapeutic dose of an imidazole compound in an amount to provide between 1.4–140 mg/kg/day while considering patient's health, weight, age and other factors which influence drug response. The drug may be administered per os or by injection, and if by injection, either by single injection, multiple injections or continuous infusion.

In the preferred process of the present invention, the imidazole compound is administered with a plasminogen activator in a combination therapy. When combination therapy is employed, it is preferable to administer the Factor XIIIa inhibitor imidazole compound first in a single bolus and thereafter to administer the plasminogen activator by continuous infusion. However, both may be administered simultaneously as a continuous infusate. Under certain circumstances it may be desirable to administer the imidazole compound subsequent to the administration of the plasminogen activator. It is intended that the method of the present invention embrace concurrent administration as well as sequential administration, in any order.

When the Factor XIIIa inhibitor imidazole compound and plasminogen activator are employed in a combination therapy, it is most desirable to use the plasminogen activator in the dose range of about 500 to 10,000 I.U./kg/minute for from about 30 to 180 minutes and the imidazole compound in the range of 1 µg–100 µg/kg/minute for a day (1440 minutes).

When the imidazole compound is to be used with a platelet aggregation inhibitor in combination therapy, the dose range for platelet aggregation inhibitor depends on the nature of the inhibitor. When the platelet aggregation inhibitor is aspirin, the aspirin may be employed at a dose of 25–325 mg twice a day. When the platelet aggregation inhibitor compound is dipyridamole, the dipyridamole may be employed at a dose of 25–100 mg four times a day. When the platelet aggregation inhibitor is a semi-synthetic peptide such as "Echistatin" or "Bitistatin", the peptide may be administered in a dose range of 0.1 to 1 nanomole/kg/min. for from 30 to 180 minutes. In each case, the imidazole compound may be employed in the range of 1–100 µg/kg/min. for a day. The administration may be carried out simultaneously or sequentially in any order as in the procedure for administration with plasminogen activators.

When the imidazole compound is to be used with heparin, heparin may be administered at doses of 4000 to 8000 units per 4 hours and the imidazole compound in the range of 1 µg–100 µg/kg/minute for a day. When it is to be used with coumarin drugs these drugs are administered orally at doses of 10 to 15 mg/kg/day and the imidazole compound administered by infusion at a rate of 1 µg–100 µg/kg/minute for a day.

Compositions to be employed in the practice of the present invention whether parenteral, oral or suppository compositions comprises an imidazole compound in a pharmaceutically acceptable carrier.

Parenteral compositions comprise the imidazole compound in sterile physiologically acceptable media such as physiological saline. Such compositions may also contain other ingredients for purposes such as for aiding solubility or for preservation or the like, said ingredients being those acceptable for intravenous administration. The compositions may be prepared as concentrate compositions and lyophilized and then diluted to the appropriate treating composition immediately prior to administration. A therapeutic composition as a unit dose form may contain from 100 mg to 10 grams of imidazole compound. Compositions suitable in the preferred practice of the present invention of co-administering plasminogen activator and Factor XIIa inhibitor compound may contain (a) about 58 million I.U. of tissue plasminogen activator (tPA) or 1.5 million I.U. of streptokinase and (b) from 100 mg to 10 grams of the imidazole compound.

Oral compositions also may be prepared with the active ingredient in admixture with a pharmaceutically acceptable carrier. Suitable carriers for liquid compositions include water, glycols, oils, alcohols, flavoring agents, preservatives, coloring agents and the like; for solid preparations, starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

Suppository compositions may be prepared with ointments, jellies, carbowax, polyethylene sorbitan monostearate, polyethylene glycol, cocoa butter, and other conventional carriers.

The preparation of the imidazole compounds suitable for inhibiting transglutaminase enzymes, particularly Factor XIIIa, and compositions suitable for carrying out the process of the present invention are illustrated by the following examples but are not to be construed as limiting.

EXAMPLE I

Procedure A

A. 1-Methyl-5-phenyl-2[(2-oxopropyl)thio]imidazole

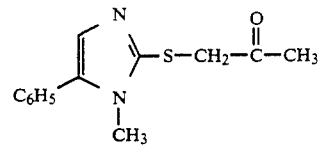

To a solution of 4.76 g (0.025 mol) of 1-methyl-5-phenyl-imidazol-2-thiol and 3.15 g (0.031 mol) of triethylamine in 250 mL of acetone was added 2.55 g (0.28 mol) of chloroacetone in 250 mL of acetone. The solution was stirred at room temperature for 16 hours. The acetone was removed by evaporation and the residue was partitioned between ethyl acetate and water. The ethyl acetate phase was washed with water, brine, and dried over magnesium sulfate. The solvent was evaporated from the dried solution to obtain as residue 6.16 grams of 1-methyl-5-phenyl-2[(2-oxopropyl)thio]imidazole which was purified by flash chromatography on silica gel using 2 percent methanol in chloroform as eluant.

B.
1,3-Dimethyl-4-phenyl-2-[(2-oxopropyl)thio]-1H-imidazolium chloride

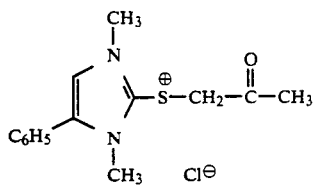

To a solution of 0.25 gram (0.001 mol) of the 1-methyl-5-phenyl-2[(2-oxopropyl)thio]imidazole, prepared as above described, in 10 mL of methylene chloride was added 0.164 g (0.001 mol) of methyl trifluoromethanesulfonate, and the solution was stirred overnight at room temperature. The solvent was evaporated and the residue was converted to the chloride ion form by dissolving in 20% methanol/water and passing through Dowex-1 (Cl$^-$)ion exchange column. The column was eluted with 20 percent methanol in water and the eluate subjected to reduced pressure to evaporate the solvent and to obtain a residue. The residue was stirred overnight in ethyl acetate, filtered and recrystallized from isopropanol/hexane to obtain purified 1,3-dimethyl 4-phenyl-2[(2-oxopropyl)thio]-1H-imidazolium chloride, m.p. 143°-146° C.

Anal. Cald for $C_{14}H_{17}ClN_2OS.1/6H_2O$: C, 56.08; H, 5.83; N, 9.34. C, 56.08; H, 5.92; N, 9.28.

EXAMPLE II
Procedure B

A.
1-Methyl-4,5-diphenyl-2[(2-oxopropyl)thio]-imidazole

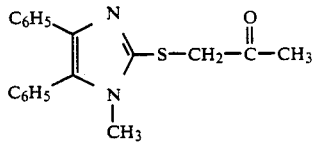

1-Methyl-4,5-diphenylimidazol-2-thiol was first prepared as follows: 10.0 grams (0.047 mol) of benzoin and 4.25 grams methylthiourea were stirred together in 50 milliliters of hexanol-1 and heated to reflux and the refluxing continued for about 20 hours. The mixture was allowed to cool whereupon crystals formed in the reaction mixture. The crystals were recovered by filtration and purified on a silica gel column to obtain 0.68 gram of 1-methyl-4,5-diphenylimidazol-2-thiol, m.p. 280°-283° C.

The 1-methyl-4,5-diphenylimidazol-2-thiol (0.618 g, 0.00255 mol) was dissolved in 150 milliliters of acetone and to it was added with stirring 0.236 gram (0.00255 mol) of chloroacetone and 0.258 g (0.00255 mol) of triethylamine. The mixture was stirred overnight at room temperature. Since the reaction was not complete as determined by TLC, 0.25 gram of chloroacetone and 0.26 gram of triethylamine was added and the mixture refluxed for one hour. The mixture was then allowed to cool and evaporated in vacuo to obtain a residue. The latter was dissolved in ethyl acetate, the ethyl acetate solution was washed with water, 5% sodium hydroxide and brine, the washed solution was dried (MgSO$_4$), and the dried solution evaporated in vacuo to obtain a still impure product. The latter was put over a silica gel column and developed with 1 percent methanol in methylene chloride to recover from the eluate after evaporating off the solvent, 0.561 gram of 1-methyl-4,5-diphenyl-2[(2-oxo-propyl)thio]imidazole. The product after recrystallization from isopropyl alcohol-hexane had a melting point of 179°-182° C.

Anal. Calcd. for $C_9H_{18}N_2OS.HCl$ C, 63.58; H, 5.34; N, 7.81. Found C, 63.56; H, 5.37; N, 7.61.

B.
1,3-Dimethyl-4,5-diphenyl-2[(2-oxopropyl)thio]-1H-imidazolium trifluoromethanesulfonate

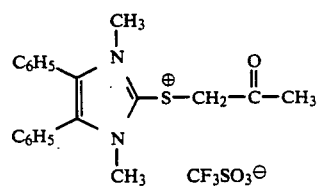

0.561 gram (0.00174 mol) of the imidazole prepared in part A was dissolved in 15 milliliters of methylene chloride and while stirring at room temperature there was added 0.31 g of methyl trifluoromethanesulfonate. The resulting mixture was stirred one hour, then an additional 0.3 gram of methyl trifluoromethanesulfonate was added and stirred for 2 hours. The mixture was coevaporated with isopropanol to obtain crystals of the desired imidazolium trifluoromethanesulfonate which after crystallization from isopropanol had a melting point of 138°-139° C.

Anal. Calcd for $C_{21}H_{21}N_2F_3O_4S_2$: C, 51.84; H, 4.35; N, 5.76. Found: C, 51.61; H, 4.62; N, 5.72.

EXAMPLE III

A. 1-Methyl-2[(2-oxopropyl)thio]benzimidazole

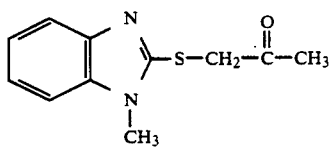

1-Methylbenzimidazole-2-thiol starting material was prepared by the procedure of G. F. Duffin et al., J. Chem. Soc. 361 (1956) from 14.2 grams of N-methyl-nitro-aniline by reducing with zinc and alkali in ethanol to obtain N-methyl-o-phenylenediamine and intimately contacting the latter with carbon disulfide to obtain 6.1 grams of 1-methylbenzimidazole-2-thiol, m.p. 192°-193° C.

To 1.0 gram (0.0061 mol) of 1-methyl-benzimidazole-2-thiol in 50 milliliters of acetone was added 0.64 g (0.0069 mol) of chloroacetone; then 0.71 gram (0.007 mol) of triethylamine was added dropwise with stirring and the stirring continued overnight at room temperature. The mixture was then evaporated in vacuo and the residue dissolved in 100 milliliters of ethyl acetate. The ethyl acetate solution was washed successively with water, 5 percent sodium hydroxide and water and dried over MgSO$_4$. Ethyl acetate was vaporized from the dried solution to obtain as residue 1.4 grams of the thiol compound which was further purified by recrystallizing from butyl chloride, chromatographing over silica gel with chloroform and recrystallizing from butyl chloride to obtain 150 mg of the desired 1-methyl-2[(2-oxopropyl)thio]benzimidazole, m.p. 87°-88° C.

Anal. Calcd, for C$_{11}$H$_{12}$N$_2$OS: C, 59.97; H, 5.49; N, 12.72. Found: C, 59.83; H, 5.55; N, 12.54.

B.
1,3-Dimethyl-2-[(2-oxopropyl)thio]-1H-benzimidazolium trifluoromethanesulfonate 0.340 gram (0.00154 mol) of the benzimidazole above prepared was dissolved in 10 milliliters of methylene chloride and to the resulting solution was added 0.30 gram (0.00154 mol) of methyl trifluoromethanesulfonate and the mixture stirred for three hours at room temperature. The mixture was then subjected to reduced pressure to remove the solvent and to obtain the imidazolium salt product as residue. The product was crystallized from isopropyl alcohol to obtain, after drying, a purified product melting 130°-132° C.

Anal. Calcd for C$_{13}$H$_{15}$F$_3$N$_2$O$_4$S$_2$: C, 40.62; H, 3.93; N, 7.29. Found: C, 40.47; H, 4.24; N, 7.29.

EXAMPLE IV

4-Chloro-1,3-dimethyl-2-[(2-oxopropyl)thio]-1H-imidazolium chloride

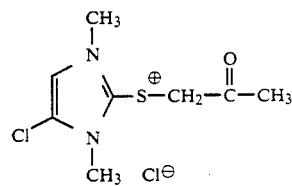

The starting material, 4-chloro-1,3-dimethylimidazoline-2-thione was first prepared by adding dropwise and intimately admixing 5.68 grams (0.04 mol) of methyl iodide to a solution of 4.0 grams (0.0343 mol) of 5-chloro-1-methylimidazole in 25 milliliters of methylene chloride. The resulting mixture was stirred overnight at room temperature whereupon a crystalline product was found to have formed. The latter was recovered with cold methylene chloride to obtain 1,3-dimethyl-5-chloroimidazolium chloride.

The imidazolium chloride thus obtained (3.65 grams, 0.0141 mol), 0.45 gram (0.0141 gram atom) sulfur, and 2.44 grams (0.0178) moles of potassium carbonate and 25 milliliters of anhydrous methanol were stirred vigorously overnight at room temperature. Thereafter, the mixture was filtered and the filtrate evaporated to dryness. The residue was recrystallized from water to obtain 4-chloro-1,3-dimethylimidazoline-2-thione which was used in the preparation of the oxopropylthioimidazolium salt.

To a solution of 1.00 gram (0.0062 mol) of 4-chloro-1,3-dimethyl-imidazoline-2-thione in 180 mL of acetone was added 0.569 g (0.0062 mol) of chloroacetone and a small crystal of sodium iodide. The mixture was stirred overnight at room temperature whereupon a product precipitated. The latter was recovered by filtration and recrystallized from isopropyl alcohol-hexane to obtain purified 4-chloro-1,3-dimethyl-2[-(2-oxopropyl)thio]-1H-imidazolium chloride, m.p. 134°-136° C.

Anal. Calcd, for C$_8$H$_{12}$ClN$_2$OS: C, 37.65; H, 4.74; N, 10.95. Found: C, 37.65; H, 4.58; N, 11.03.

EXAMPLE V 1,3-Dimethyl-4-(methylaminocarbonylamino)-2-[(2-oxopropyl)thio]-1H-imidazolium chloride

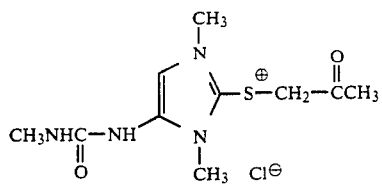

To a solution of 3.22 grams (0.0225 mol) of 1,3-dimethyl-4-amino-4-imidazoline-2-thione (prepared from methylaminoacetonitrile and methyl isothiocyanate by the method of T. Kinoshita et al, Bull. Chem. Soc. Japan., 53, 442 (1980)) in 12 mL of pyridine under an atmosphere of nitrogen was added with stirring 2.61 grams (0.0457 mol) of methyl isocyanate. The mixture became exothermic. Stirring was continued overnight whereupon a solid precipitate formed in the reaction mixture. The latter was collected by filtration and washed with isopropyl alcohol to obtain 2.11 grams of 1,3-dimethyl-4-(methylaminocarbonylamino)-imidazoline-2-thione, m.p. 200°-201° C.

A solution of 0.50 gram (0.0025 mol) of the thione intermediate in 60 mL of acetone was intimately mixed with 0.28 gram of chloroacetone. A small crystal of potassium iodide was added and the solution was stirred for three days whereupon a white solid formed in the reaction mixture. The latter was collected a recrystallized from ethanol to obtain purified 1,3-dimethyl-4-(methylaminocarbonylamino)-2-[(2-oxopropyl)thio]-1H-imidazolium chloride, m.p. 177°-179° C.

Anal. Calcd for C$_{10}$H$_{17}$ClN$_4$O$_2$S: C, 41.02, H, 5.85; N, 19.14. Found: C, 40.86; H, 5.80; N, 18.87.

EXAMPLE VI 1,3-Dimethyl-4-(acetylamino)-2-[(2-oxopropyl)thio]-1H-imidazolium chloride

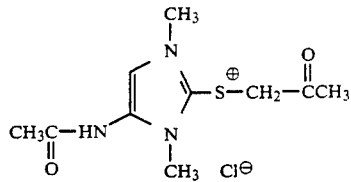

0.50 gram (0.0027 mol) of 1,3-dimethyl-4-(acetylamino)-imidazoline-2-thione (prepared by acetylating by conventional means the 1,3-dimethyl-4-amino-4-imidazoline-2-thione described in Example V) and 0.28 gram (0.003 mol) of chloroacetone were mixed together and refluxed for two hours after which time a solution 0.428 gram of sodium iodide in 5 milliliters of acetone was added whereupon a reaction took place with the immediate formation of a precipitate of sodium chloride by-product. The latter was removed by filtration and the filtrate evaporated to dryness to obtain a residue. The residue was dissolved in acetone and from the solution was recovered a solid which after purification on a Dowex-1 (Cl$^-$) column and crystallization from isopropyl alcohol was obtained the desired 1,3-dimethyl-4-(acetylamino)-2[(2-oxopropyl)-thio]-1H-imidazolium chloride, m.p. 171°-173° C.

Anal. Calcd, for $C_{10}H_{16}ClN_3O_2S$: C, 43.24; H, 5.81; N, 15.13. Found: C, 43.21; H, 5.68; N, 15.09.

EXAMPLE VII 1,3-Dimethyl-4,5-bis(methoxyphenyl)-2-[(2-oxopropyl)thio]-1H-imidazolium chloride

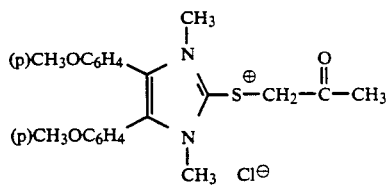

1,3-Dimethyl-4,5-bis(p-methoxyphenyl)imidazolin-2-thione was first prepared by heating together 5.45 grams (0.02 mol) of anisoin and 2.08 grams (0.02 mol) of N,N-dimethylthiourea in 20 milliliters of 1-hexanol under an atmosphere of nitrogen.

In an operation carried out in a manner similar to the preceeding examples, 0.185 gram of chloroacetone was added to a solution of 0.68 gram (0.002 mole) of the imidazolidinethione in 20 milliliters of acetone and the mixture allowed first to stand at room temperature, then refluxed for 3 hours. Thereafter, a sodium iodide crystal was added, 0.085 gram (0.002 mole) chloroacetone added and the mixture heated to obtain the desired 1,3-dimethyl-4,5-bis(p-methoxyphenyl)-2[(2-oxopropyl)-thio]-1H-imidazolium chloride, which after a series of recrystallizations was obtained as a product melting 179°–180° C.

Anal. Calcd for $C_{22}H_{25}ClN_2O_3S$: C, 61.03; H, 5.82; N, 6.47. Found: C, 60.80; H, 5.61; N, 6.64.

EXAMPLE VIII 1,3-Dimethyl-4,5-decamethylene-2-[(2-oxopropyl)thio]-1H-imidazolium chloride

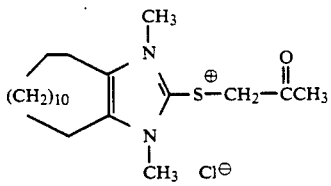

1,3-Dimethyl-4,5-decamethylene-imidazolin-2-thione was prepared by heating together at reflux temperature 2.4 gram (0.012 mol) of 2-hydroxycyclododecanone and 1.47 grams (0.014 mol) of 1-methyl-2-thiourea in 10 milliliters of hexanol. After heating for about 20 hours, the mixture was cooled, isopropanol added and chilled to obtain the imidazolin-2-thione.

In a manner similar to that previously described, 0.553 gram (0.002 mole) of the thione above prepared and 0.185 gram (0.002 mole) of chloroacetone were stirred together in 10 milliliters of acetone at room temperature; then sodium iodide crystal was added and the mixture heated to obtain the desired 1,3-dimethyl-4,5-decamethylene-2-[(2-oxopropyl)thio]-1H-imidazolium chloride, m.p. 73°–78° C.

Anal. Calcd for $C_{18}H_{31}ClN_2OS$: C, 60.22; H, 8.71; N, 7.81. Found: C, 60.13; H, 8.96; N, 8.01.

EXAMPLE IX 1,3-Dimethyl-4-([(L)-phenylalanyl]amino)-2-[(2-oxopropyl)thio]-1H-imidazolium chloride hydrochloride

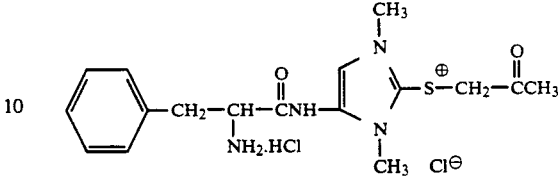

1,3-Dimethyl-4([(L)-N-(t-butyloxycarbonyl)-phenylalanyl]amino)-4-imidazoline-2-thione of the following formula

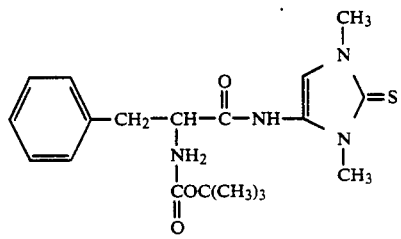

was first prepared: To a solution of 2.8 g (0.0208 mol) of 1-hydroxybenztriazole and 3.99 g (0.0208 mol) of 1-(3-dimethylaminopropyl)-3-ethylcarbodiimide hydrochloride in 30 mL of dimethylformamide was added 5.05 g (0.019 mol) of t-butyloxycarbonylphenylalanine. To this stirred solution was added dropwise over 15 minutes, a solution of 2.47 g (0.0173 mol) of 1,3-dimethyl-4-amino-4-imidazoline-2-thione (prepared from methylaminoacetonitrile and methyl isocyanate as described in Bull. Chem. Soc. Japan 53, 442 (1980)). The pH of the solution was adjusted to approximately 8.5 by the addition of 7 mL of triethylamine. The mixture was stirred for 3 hours at room temperature under a nitrogen atmosphere, and then was poured onto 500 mL of water. The aqueous solution was extracted with five 75 mL portions of ethyl acetate. The combined extracts were washed with five 100 mL portions of water, dried over MgSO4, filtered, and the ethyl acetate removed under reduced pressure. The residue was recrystallized from ethanol to obtain 4.15 g (61%) of 1,3-dimethyl-4-([(L)-N-(t-butyloxycarbonyl)phenylalanyl]amino)-4-imidazoline-2-thione as a white, crystalline material, m.p. 168°–169° C.

1,3-Dimethyl-4-([(L)-phenylalanyl]amino)-2-[(2-oxopropyl)thio]imidazolium chloride hydrochloride was then prepared: To a solution of 0.050 g (0.00128 mol) of the thione above prepared in 12 mL of acetone was added 0.12 g (0.0013 mol) of chloroacetone, and the solution was stirred 3 days. Additional chloroacetone (0.5 mL) was added at this time and the solution was stirred and refluxed for 24 hours. The solution was concentrated under vacuum and the residue was stirred with 5 mL of ethanol saturated with HCl (gas) for 6 hours. The solution was concentrated under vacuum and the residue was crystallized from isopropyl alcohol ether to obtain the desired 1,3-dimethyl-4-([(L)-phenylalanyl]amino)-2-[(2-oxopropyl)thio]-1H-imidazolium chloride hydrochloride; m.p. indeterminate at 90°–100° C. (softens, then foams).

Anal. Calcd for $C_{17}H_{23}ClN_4O_2S \cdot HCl \cdot 2H_2O$: C, 44.83; H, 6.20; N, 12.30. Found: C, 44.36; H, 5.63; N, 12.02.

EXAMPLE X

1-Benzyl-3-methyl-2-[(2-oxopropyl)thio]-1H-imidazolium chloride

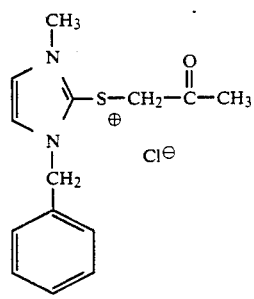

1-Benzyl-3-methylimidazoline-2-thione was first prepared as follows: 8.93 grams of methyl iodide was added slowly with stirring to 10.0 grams of benzylimidazole in 25 milliliters of methylene chloride. The mixture was stirred for three hours and then an additional 2.0 grams of methyl iodide was added. The mixture was then evaporated to dryness in vacuo to obtain 18.97 grams of an residue of 1-benzyl-3-methylimidazolium iodide.

The quaternary salt thus obtained was then stirred together at room temperature with 10.92 grams of anhydrous potassium carbonate, 2.03 grams of powdered sulfur and 100 milliliters of anhydrous methanol for about 48 hours. Thereafter, the mixture was filtered through a pad of celite and washed with 200 milliliters of methylene chloride. The filtrate was evaporated to dryness in vacuo and the residue boiled with 100 milliliters of water. The residue was recrystallized from 100 milliliters of absolute methanol to obtain purified 1-benzyl-3-methylimidazoline-2-thione.

1-Benzyl-3-methyl-2-[(2-oxopropyl)thio]-1H-imidazolium chloride was prepared as follows: 0.5 gram of chloroacetone was added with stirring to a solution of 1.0 gram of the thione above prepared in 20 milliliters of acetone. A very small crystal of sodium iodide was added and the mixture stirred overnight at room temperature. A small amount of crystalline material precipitated. The mixture was then heated at reflux temperature for 18 hours to obtain a crystalline product. The latter was recovered, washed with acetone and recrystallized from a 10 milliliter isopropyl alcohol-20 milliliter ether mixture to obtain purified 1-benzyl-3-methyl-2-[(2-oxo-propyl)thio]-1H-imidazolium chloride, m.p. 119°-121° C.

Anal. Calcd for $C_{14}H_{17}ClN_2OS \cdot 0.25H_2O$: C, 55.21; H, 5.76; N, 9.16. Found: C, 55.39; H, 5.59; N, 9.14.

EXAMPLE XI 1-(3-Methoxy-3-oxopropyl)-3-methyl-2-[(2-oxopropyl)thio]-1H-imidazolium chloride

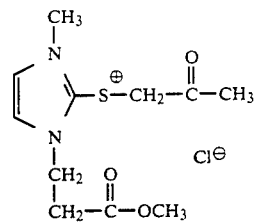

In operations carried out in a manner similar to that described in Example I, 1-(3-methoxy-3-oxopropyl)imidazol-2-thiol was reacted first with chloroacetone and triethylamine to obtain 1-(3-methoxy-3-oxopropyl)-3-methyl-2-[(2-oxopropyl)thio]-1H-imidazole, which then was reacted with methyl trifluoromethanesulfonate to obtain 1-(3-methoxy-3-oxopropyl)-3-methyl-2-[(2-oxopropyl)thio]-1H-imidazolium trifluoromethanesulfonate, which in turn was passed through a Dowex-1 (Cl⁻) ion exchange column to obtain 1-(3-methoxy-3-oxopropyl)-3-methyl-2-[(2-oxopropyl)thio]-1H-imidazolium chloride having m.p. 121°-124° C.

Anal. Calcd for $C_{11}H_{17}ClN_2O_3S$: C, 45.12; H, 5.85; N, 9.57. Found: C, 45.24; H, 5.76; N, 9.45.

EXAMPLE XII 1-(3-Amino-3-oxopropyl)-3-methyl-2[(2-oxopropyl)thio]-1H-imidazolium chloride

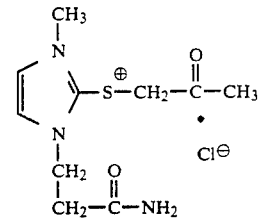

In operations carried out in a manner similar to that described in Example I, 1-(3-amino-3-oxopropyl)imidazol-2-thiol was reacted first with chloroacetone in the presence of triethylamine to obtain 1-(3-amino-3-oxopropyl)-3-methyl-2[(2-oxopropyl)thio]-1H-imidazole, which then was reacted with methyl trifluoromethanesulfonate to obtain 1-(3-amino-3-oxopropyl)-3-methyl-2[(2-oxopropyl)thio]-1H-imidazolium trifluoromethanesulfonate which in turn was passed through a Dowex 1(Cl⁻) ion exchange column to obtain 1-(3-amino-3-oxopropyl)-3-methyl-2[(2-oxopropyl)thio]-1H-imidazolium chloride, m.p. 124°-125° C.

Anal. Calcd for $C_{10}H_{16}ClN_3O_2S$: C, 43.24; H, 5.81; N, 15.13. Found: C, 42.96; H, 5.80; N, 14.95.

EXAMPLE XIII 1,3-Dimethyl-4,5,6,7-tetrahydro-2-[(2-oxopropyl)thio]-1H-benzimidazolium Chloride

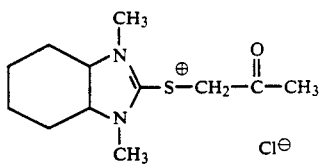

1,3-Dimethyl-[4,5,6,7-tetrahydro-2-thionobenzimidazole] was first prepared by heating together at reflux temperature 11.41 grams (10.0 mmols) of 2-hydroxycyclohexanone and 10.42 grams (0.014 mol) of N,N'-dimethylthiourea in 10 milliliters of hexanol under argon atmosphere for 24 hours. The mixture was subjected to reduced pressure to remove the volatiles, isopropanol then was added and the resulting mixture chilled to obtain a yellow solid which after filtration and drying amounted to 10.0 grams of the imidazolin-2-thione.

A solution of 4.00 grams (22.0 mmol) of the thione above prepared in 110 mL of acetone was stirred at 25° C. while 2.0 grams (22.0 mmol) of chloroacetone was added. After 18 hours an additional 2.0 grams of chloroacetone was stirring continued. This was repeated with three more portions of chloroacetone. The resulting mixture was concentrated to obtain a solid which was then triturated with ethyl acetate and recrystallized from isopropyl alcohol and ethyl acetate to obtain 4.00 grams of the desired 1,3-dimethyl-4,5,6,7-tetrahydro-2-[(2-oxopropyl)thio]-1H-benzimidazolium chloride, m.p. 149°–151° C.

EXAMPLE XIV

In operations carried out in a manner similar to that described in Examples VIII–X, the compounds in Table II are prepared:

(1) 1-[2-(p-Propylphenyl)ethyl]-2[(2-oxopropyl)thio]-1H-imidazole;

1-[2(p-Propylphenyl)ethyl]-3-methyl-2-[(2-oxopropyl)thio]-1H-imidazolium trifluoromethanesulfonate;

1-[2(p-Propylphenyl)ethyl]-3-methyl-2[(2-oxopropyl)thio]-1H-imidazolium chloride.

(2) 1-[3-(p-Chlorophenyl)propyl]-2-[(2-oxopropyl)thio]-1H-imidazole;

1-[3-(p-Chlorophenyl)propyl]-2-[(2-oxopropyl)thio]-1H-imidazolium trifluoromethanesulfonate;

1-[3-(p-Chlorophenyl)propyl]-2-[(2-oxopropyl)thio]-1H-imidazolium chloride.

(3) 1-Isopropyl-2-[(2-oxopropyl)thio]-1H-imidazole;

1,3-Diisopropyl-2-[(2-oxopropyl)thio]-1H-imidazolium trifluoromethanesulfonate;

1,3-Diisopropyl-2-[(2-oxopropyl)thio]-1H-imidazolium chloride.

EXAMPLE XVI

In operations carried out in a manner similar to that described in Example I, the compounds in Table II are prepared:

TABLE II

| R | $R^1$ | $R^2$ | $R^3$ | $R^4$ | Salt |
|---|---|---|---|---|---|
| —CH₂CH₂CH₃ | —CH₃ | —Cl | H | —CH₃ | CF₃SO₃⁻ |
| —CH₂CH₂OH | —CH₃ | —CN | H | —CH₃ | CF₃SO₃⁻ |
| —CH₂OCH₂CH₃ | —CH₃ | —NO₂ | H | —CH₃ | CF₃SO₃⁻ |
| —CH₂CH₂COOCH₃ | —CH₃ | —C₆H₅ | H | —CH₃ | CF₃SO₃⁻ |
| —CH₂CONH₂ | —CH₂CH₃ | —OC₂H₅ | H | —CH₂CH₃ | Cl⁻ |
| —CH₂CN | —C₃H₇ | —C₆H₅Cl(p) | H | —C₃H₇ | CF₃SO₃⁻ |
| —CH₂C₆H₅ | —CH₃ | —COOCH₃ | H | —CH₃ | Cl⁻ |
| —C₆H₅ | —CH(CH₃)₂ | —C₆H₅ | H | —CH(CH₃)₂ | CF₃SO₃⁻ |
| —C₆H₄OCH₃(p) | —CH₃ | —(CH₂)₄— |  | —CH₃ | CF₃SO₃⁻ |
| —C₆H₄OCH₃(o) | —CH₃ | —CN | H | —CH₃ | CF₃SO₃⁻ |
| —C₆H₄OH(p) | —CH₂CH₃ | —C₆H₅ | C₆H₅ | —CH₂CH₃ | Cl⁻ |
| —C₆H₄COOCH₃ | —CH₃ | (benzo-fused) |  | —CH₃ | Cl⁻ |
| —C₆H₄CN | —CH₃ | —SC₆H₅ | H | —CH₃ | Cl⁻ |
| —C₆H₄CONHCH₃ | —CH₃ | —C₆H₅Br(p) | H | —CH₃ | Cl⁻ |
| —(CH₂)₅CH₃ | —C₂H₄C₆H₅ | —Cl | H | —CH₃ | CF₃SO₃⁻ |
| —C₆H₄CONH₂ | —C₂H₄CONH₂ | —CN | H | —CH₃ | CF₃SO₃⁻ |
| —CH₂CH₂Cl | —C₂H₄COOCH₃ | —NO₂ | H | —CH₃ | CF₃SO₃⁻ |
| —CH (CH₂)₅ | —CH₃ | —C₆H₄OCH₃(p) | H | —CH₃ | CF₃SO₃⁻ |
| —CH₂C₆H₄Br(p) | —CH₃ | (benzo-fused) |  | —CH₃ | CF₃SO₃⁻ |
| —CH₂C₆H₄OH(o) | —CH₃ | —(CH₂)₄— |  | —CH₃ | CF₃SO₃⁻ |
| —CH₂C₆H₄OCH₃ | —CH₃ | —(CH₂)₃— |  | —CH₃ | CF₃SO₃⁻ |

TABLE II-continued

| R | R$^1$ | R$^2$ | R$^3$ | R$^4$ | Salt |
|---|---|---|---|---|---|
| 2-pyridyl | —CH$_3$ | —CH$_2$OH | H | —CH$_3$ | CF$_3$SO$_3$$^-$ |
| 2-pyrimidinyl | —CH$_3$ | —Cl | H | —CH$_3$ | CF$_3$SO$_3$$^-$ |
| 2-pyrazinyl | —CH$_3$ | —C$_6$H$_5$ | H | —CH$_3$ | CF$_3$SO$_3$$^-$ |

EXAMPLE XVII

In operations carried out in a manner similar to the foregoing examples, the following compounds are prepared:

EXAMPLE XVIII

The following compounds are prepared by intimately mixing the imidazole with ethanolic hydrogen chloride, letting the mixture stand at ambient temperature to allow the crystals of the salt to form and then recovering by filtration.

TABLE III

| R | R$^1$ | R$^2$ | R$^3$ | R$^4$ | Salt |
|---|---|---|---|---|---|
| —CH$_3$ | —CH$_3$ | —NHCOC$_3$H$_7$ | H | —CH$_3$ | Cl$^-$ |
| —C$_2$H$_5$ | —CH$_3$ | —CH(NH$_2$)CH$_2$C$_6$H$_5$ | H | —CH$_3$ | Cl$^-$ |
| —CH$_3$ | —CH$_3$ | —NHCH$_3$ | H | —CH$_3$ | CF$_3$SO$_3$$^-$ |
| —CH$_3$ | —CH$_3$ | —CH(OH)C$_6$H$_5$ | H | —CH$_3$ | CF$_3$SO$_3$$^-$ |
| —H | —CH$_3$ | —CH(OH)C$_6$H$_5$OCH$_3$(p) | H | —CH$_3$ | Cl$^-$ |
| —CH$_3$ | —CH$_3$ | —CH(OH)C$_6$H$_4$C$_6$H$_5$(p) | H | —CH$_3$ | CF$_3$SO$_3$$^-$ |
| —CH$_3$ | —CH$_3$ | —C(OH)(C$_6$H$_5$)$_2$ | H | —CH$_3$ | Cl$^-$ |
| —H | —CH$_3$ | —CH(OH)C$_6$H$_4$CH$_3$(p) | H | —CH$_3$ | CF$_3$SO$_3$$^-$ |
| —CH$_3$ | —CH$_3$ | —CH(OH)(2-thienyl) | H | —CH$_3$ | Cl$^-$ |
| —CH$_3$ | —CH$_3$ | —C(OH)(cyclohexyl) | H | —CH$_3$ | CF$_3$SO$_3$$^-$ |
| —H | —CH$_3$ | —CH$_2$—CH(COCH$_3$)—CH$_2$OCH$_3$ | H | —CH$_3$ | Cl$^-$ |
| —H | —CH$_3$ | —CH$_2$CH(OC$_6$H$_5$)CH$_2$OC$_6$H$_5$ | H | —CH$_3$ | Cl$^-$ |
| —H | —CH$_3$ | —CH$_2$—CH(OCOC$_6$H$_4$OC$_6$H$_5$(p))—CH$_2$OCH$_3$ | H | —CH$_3$ | CF$_3$SO$_3$$^-$ |

1-Methyl-5-phenyl-2[(2-oxopropyl)thio]imidazole hydrochloride.

1-Methyl-4,5-diphenyl-2[(2-oxopropyl)thio]imidazole hydrochloride.

5-Chloro-1-methyl-2-[(2-oxopropyl)thio]imidazole hydrochloride.

1-Methyl-5-(methylaminocarbonylamino)-2-[(2-oxopropyl)thio]imidazole hydrochloride.

EXAMPLE XIX

In a similar manner the following salts are prepared by mixing the imidazole with an ethanolic solution of the acid corresponding to the salt desired:

1-Ethyl-4,5-diphenyl-2[(2-oxopropyl)thio]imidazole hydrogen maleate.

5-Chloro-1-methyl-2[(2-oxopropyl)thio]imidazole hydrogen citrate.

EXAMPLE XX 1,3,4,5-Tetramethyl-2-[(3-phenoxy-2-oxopropyl-thio)]-1H-imidazolium chloride 1-Chloro-3-phenoxy-propan-2-one was prepared by the method of R. Longoni, P. Berntsson, N. Bild, and M. Hesse, Hlev. CHim. Aeta, 60, 103 (1977) and/or K. J. Stevenson and L. B. Smillie, Canadian Journal of Biochemistry, 46, 1357 (1968). In the preparation, 8.0 grams phenoxyacetyl chloride was added dropwise to a cooled (ice bath) solution of about 3.0 grams of diazomethane in 60 milliliters of ether to obtain an intermediate 1-diazo-3-phenoxypropan-2-one. Hydrogen chloride was bubbled into the resulting mixture whereupon nitrogen evolution occurred with the formation of 1-chloro-3-phenoxy-propan-2-one which was recovered by conventional procedures.

To a solution of 0.50 g (0.0032 mol) of 1,3,4,5-tetramethylimidazoline-2-thione in 25 mL of acetone was added 0.59 g (0.0032 mol) of 1-chloro-3-phenoxy-propan-2-one and the solution was stirred overnight at room temperature. The product that crystallized was collected by filtration. Recrystallization from iso-propyl-alcohol-ether gave 1,3,4,5-tetramethyl-2-[(3-phenoxy-2-oxo-propyl)thio)]-1H-imidazolium chloride, m.p. 156°–157°.

Anal. Calcd for $C_{16}H_{21}N_2O_2S$: C, 56.37; H, 6.21; N, 8.22. Found: C, 55.98; H, 6.24; N, 8.05.

EXAMPLE XXI

1-Benzyl-3-methyl-2-[(3-phenoxy-2-oxopropyl)thio]-1H-imidazolium chloride

The above-identified compound, m.p. 110°–112° C. was prepared in substantially the same manner as described in Example XX from 1-chloro-3-phenoxy-propan-2-one and 1-benzyl-3-methyl-imidazolium-2-thione.

EXAMPLE XXII 1,3-Dimethyl-2-{[3-(2-pyridinyl-N-oxide thio)-2-oxopropyl]thio}-1H-imidazolium chloride 0.51 g (0.002 mol) of 1,3-dimethyl-2-[(3-chloro-2-oxopropyl)thio]-1H-imidazolium chloride was added to a solution of 0.30 g (0.002 mol) of 2-mercaptopyridine N-oxide sodium salt hydrate in 6 mL of absolute ethanol. The resulting mixture was stirred at room temperature for 7.5 hours whereupon a white precipitate formed. It was removed by filtration and recrystallized from isopropyl alcohol-ethanol to obtain 1,3-dimethyl-2-{[3-(2-pyridinyl-N-oxide thio-2-oxopropyl]thio}-1H-imidazolium chloride, m.p. 194° (dec).

Anal. Calcd for $C_{13}H_{16}ClN_3O_2S_2$: C, 40.94; H, 4.23; N, 11.02; Found: C, 41.01; H, 4.13; N, 11.19;

EXAMPLE XXIII

One liter of a parenteral composition comprising one of the foregoing compounds may be prepared from the following formulation:

|  | Grams |
| --- | --- |
| Imidazolium salt | 5.0 |
| Polysorbate 80 | 2.0 |
| Sodium chloride | 9.0 |
| Sodium carboxymethylcellulose | 10.00 |
| Methyl paraben | 1.8 |
| Propyl paraben | 0.2 |
| Water, USP | q.s. to 1 liter |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

EXAMPLE XXIV

Oral Composition 5000 compressed tablets, each containing as active ingredient 100 milligrams of one of the foregoing compounds, may be prepared from the following formation:

|  | Grams |
| --- | --- |
| Imidazolium salt | 500 |
| Starch | 700 |
| Dibasic calcium phosphate hydrous | 5000 |
| Calcium stearate | 25 |

The ingredients are finely powdered, mixed well, and then granulated with 10 percent starch paste. The granulation is dried and compressed into tablets using starch as a disintegrant and calcium stearate as lubricant.

Preparation of the Starting Materials

A. 2-Mercaptoimidazole

The 2-mercaptoimidazoles may be obtained by a reaction between an appropriate acyloin and mono-substituted urea according to the following equation:

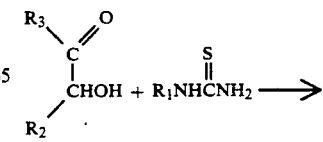

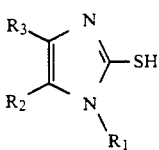

The reaction may be carried out by fusing the reactants or by refluxing the components in hexanol-1 as more fully described by Nuhn, P. et. al., J. fur praktische Chemie, 312, 90 (1970) for the fusion method and by Kjellin, G. et. al., Acta Chemica Scandinavica, 23, 2879 (1969) for the method where the α-hydroxyketones and N-alkylthioureas are refluxed in 1-hexanol with a water separator. The teachings of the foregoing articles on the preparation of the starting 2-mercaptoimidazoles are incorporated by reference.

The acyloins may be prepared in any manner within the knowledge of those skilled in the art.

B. 1,3-Disubstituted-imidazoline-2-thione 1,3-disubstituted-imidazoline-2-thione may be obtained by the reaction between an α-hydroxyketone and di-substituted thiourea according to the equation

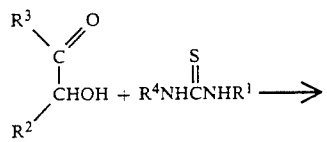

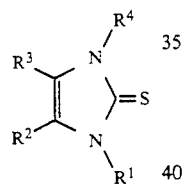

The reactants may be intimately contacted in the manner above described for the preparation of the mercaptoimidazoles.

What is claimed is:

1. A composition suitable for thrombolytic therapy in unit dosage form comprising (a) a plasminogen activator selected from tPA in an amount of about 58 million I.U. and streptokinase in an amount of 1.5 million I.U. and (b) an imidazolium salt in an amount of 100 mg to 10 grams, said imidazolium salt having the formula

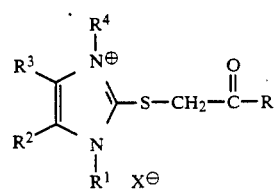

wherein
R is
   hydrogen;
   lower alkyl;
   substituted lower alkyl wherein the substituents are selected from hydroxy, lower alkoxy, phenoxy, phenylthio, 2-pyridinyl-N-oxide thio, and halo;
   cycloalkyl from 3 to 6 carbon atoms;
   benzyl;
   substituted benzyl wherein the substituents are selected from halo, hydroxy and lower alkoxy;
   phenyl;
   substituted phenyl containing 1 to 3 substituents selected from hydroxy, lower alkoxy, carbo(lower alkoxy), carbamido, N-(lower alkyl)carbamido or cyano;
   pyridyl;
   pyrimidinyl; or
   pyrazinyl
$R^1$ is
   lower alkyl
   substituted lower alkyl wherein the substituent is carbalkoxy or carbamido; or $ArC_nH_{2n}$—wherein Ar is phenyl, (lower alkyl)phenyl, (lower alkoxy)phenyl, or halophenyl and n is 1-3;
$R^2$ is
   nitro;
   carbo(lower alkoxy);
   halo;
   cyano;
   phenyl;
   substituted phenyl containing from 1 to 3 substituents selected from lower alkyl, lower alkoxy, halo and hydroxy;
   phenoxy;
   phenylthio;
   an amido group represented by —NHCOQ wherein Q is lower alkyl, —CH(NH$_2$)CH$_2$C$_6$H$_5$ or —NH(-lower alkyl);
   a hydroxyalkyl group represented by

wherein R' is hydrogen or R" wherein R" is hydrogen, phenyl, phenoxyphenyl, biphenylyl, (lower alkyl)phenyl, lower alkyl and lower cycloalkyl, or R' and R" taken together is alkylene from 4 to 6 carbon atoms; or
   an ether-alkyl group represented by

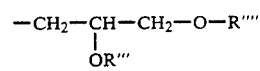

wherein R''' is hydrogen, —CO—(lower alkyl), —CO—phenyl, —CO—biphenylyl, —CO—phenyl—O—phenyl and —CONH—phenyl, and R'''' is phenyl or lower alkyl;
$R^3$ is hydrogen, or when $R^2$ is phenyl or substituted phenyl is optionally the same as $R^2$; or
$R^2$ and $R^3$ taken together is alkylene from 3 to 10 carbon atoms optionally substituted with phenyl or spiroalkylene, or benzo;
$R^4$ is lower alkyl or $ArC_nH_{2n}$ wherein Ar is phenyl, (lower alkyl)phenyl, (lower alkoxy)phenyl, or halophenyl and n is 1-3; and
X is an anion of a pharmaceutically acceptable salt;
wherein "lower" is from 1 to 6 carbon atoms inclusive; and wherein said plasminogen activator and said imidazolium salt are in a pharmaceutically acceptable carrier.

2. A composition according to claim 1 wherein the plasminogen activator is tPA.

3. A composition according to claim 1 wherein the plasminogen activator is streptokinase.

4. A method for inhibiting hard clot formation or supplementing fibrinolytic therapy comprising administering to a patient in need of such treatment an imidazolium salt and an antithrombotic agent in an amount effective for inhibiting hard clot formation or supplementing fibrinolytic therapy, said imidazolium salt having the formula

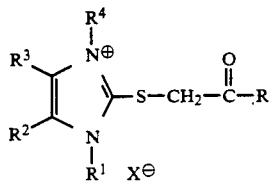

wherein
R is
  hydrogen;
  lower alkyl;
  substituted lower alkyl wherein the substituents are selected from hydroxy, lower alkoxy, phenoxy, phenylthio, 2-pyridinyl-N-oxide thio, and halo;
  cycloalkyl from 3 to 6 carbon atoms;
  benzyl;
  substituted benzyl wherein the substituents are selected from halo, hydroxy and lower alkoxy;
  phenyl;
  substituted phenyl containing 1 to 3 substituents selected from hydroxy, lower alkoxy, carbo(lower alkoxy), carbamido, N-(lower alkyl)carbamido or cyano;
  pyridyl;
  pyrimidinyl; or
  pyrazinyl
$R^1$ is
  lower alkyl
  substituted lower alkyl wherein the substituent is carbalkoxy or carbamido; or $ArC_nH_{2n}$—wherein Ar is phenyl, (lower alkyl)phenyl, (lower alkoxy)phenyl, or halophenyl and n is 1–3;
$R^2$ is
  nitro;
  carbo(lower alkoxy);
  halo;
  cyano;
  phenyl;
  substituted phenyl containing from 1 to 3 substituents selected from lower alkyl, lower alkoxy, halo and hydroxy;
  phenoxy;
  phenylthio;
  an amido group represented by —NHCOQ wherein Q is lower alkyl, —CH(NH$_2$)CH$_2$C$_6$H$_5$ or —NH(-lower alkyl);
  a hydroxyalkyl group represented by

wherein R' is hydrogen or R" wherein R" is hydrogen, phenyl, phenoxyphenyl, biphenylyl, (lower alkyl)phenyl, lower alkyl and lower cycloalkyl, or R' and R" taken together is alkylene from 4 to 6 carbon atoms; or
  an ether-alkyl group represented by

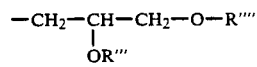

wherein R''' is hydrogen, —CO—(lower alkyl), —CO—phenyl, —CO—biphenylyl, —CO—phenyl—O—phenyl and —CONH—phenyl, and R'''' is phenyl or lower alkyl;
$R^3$ is hydrogen, or when $R^2$ is phenyl or substituted phenyl is optionally the same as $R^2$; or
$R^2$ and $R^3$ taken together is alkylene from 3 to 10 carbon atoms optionally substituted with phenyl or spiroalkylene, or benzo;
$R^4$ is lower alkyl or $ArC_nH_{2n}$ wherein Ar is phenyl, (lower alkyl)phenyl, (lower alkoxy)phenyl, or halophenyl and n is 1-3; and
X is an anion of a pharmaceutically acceptable salt;
wherein "lower" is from 1 to 6 carbon atoms inclusive.

5. A method according to claim 4 wherein the imidazolium salt is administered to provide about 1 μg to 100 μg/kg/minute for one day.

6. A method according to claim 4 wherein the antithrombotic agent is plasminogen activator.

7. A method according to claim 4 wherein the antithrombotic agent is platelet aggregation inhibitor.

8. A method according to claim 4 wherein the antithrombotic agent is an anticoagulant.

* * * * *